July 4, 1972 L. H. SHOESMITH Plant Pat. 3,225

CHRYSANTHEMUM PLANT (COPPERPLATE)

Filed Oct. 5, 1970

INVENTOR.
LEONARD H. SHOESMITH

BY Rummler & Snow
ATTYS

United States Patent Office

Plant Pat. 3,225
Patented July 4, 1972

3,225

CHRYSANTHEMUM PLANT (COPPERPLATE)

Leonard H. Shoesmith, Westfield-Woking Surrey, England, assignor to Pan-American Plant Company, Chicago, Ill.

Filed Oct. 5, 1970, Ser. No. 78,310
Int. Cl. A01h *5/00*
U.S. Cl. Plt.—79 1 Claim

ABSTRACT OF THE DISCLOSURE

A new variety of chrysanthemum plant of the decorative type suitable for pot-plant culture, distinguished by its good branching quality and profuse production of very distinctive generally copper colored or bronze-red blooms. This variety is a free breaker and produces short symmetrical plants that provide a brilliant display as a potted plant.

BACKGROUND OF THE NEW PLANT VARIETY

The new variety of chrysanthemum plant originated as a seedling selected by me from many hundreds of random crosses produced by me at West Chicago, Ill., in the course of extensive breeding efforts carried on with the object of developing improved and distinctive varieties suitable for greenhouse culture as a pot-plant. This plant was discovered in the fall of 1967 and was selected for propagation and trial because of the very distinctive coloration of its profusely produced flowers, which, in full bloom, appear to be an almost irridescent burnt orange. Asexual propagation of this plant by me at West Chicago, Ill., has showed the plant to have the advantages of being a free breaker that produces short symmetrical plants, particularly suitable for pot-time culture, as well as having a relatively short response period and the capability of being flowered at any particular time of the year.

Extensive propagation of this new variety, by vegetative cuttings, at West Chicago, Ill., and at Cortez, Fla., has demonstrated that its distinctive characteristics come true from generation to generation and appear to be firmly fixed.

DESCRIPTION OF THE DRAWINGS

This new variety of chrysanthemum plant is illustrated by the accompanying drawing in which the principal figure shows the potted plant in full bloom and in full color, as nearly true as it is reasonably possible to obtain by conventional photographic processes, the ink drawn figures show the configuration of typical leaves of the new plant and color patch is a hand-painted strip having the true burnt orange color of the flowers shown.

DESCRIPTION OF THE NEW PLANT

Figure 1:
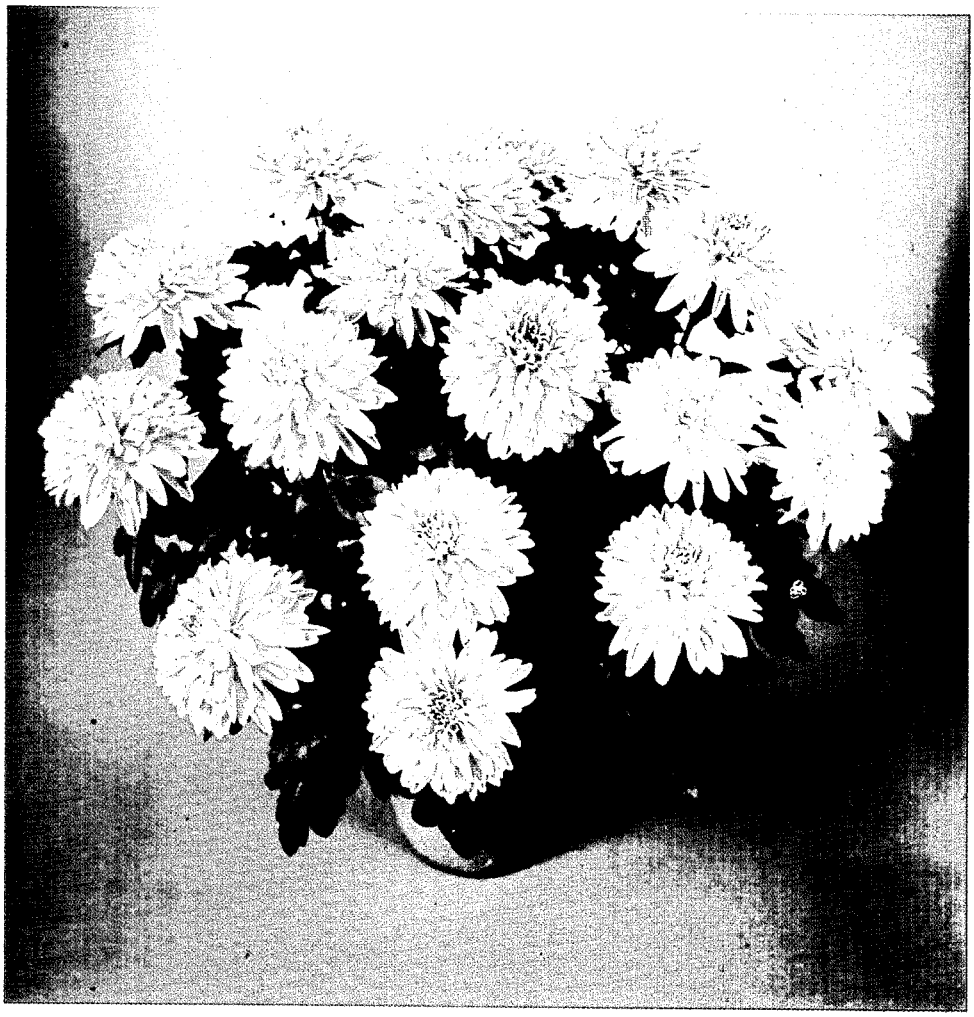
Figure 2:
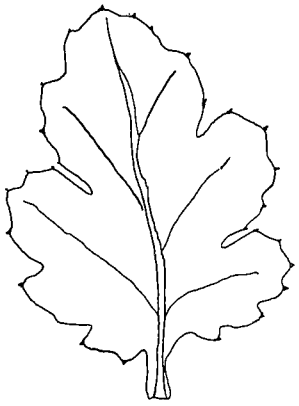
Figure 3:
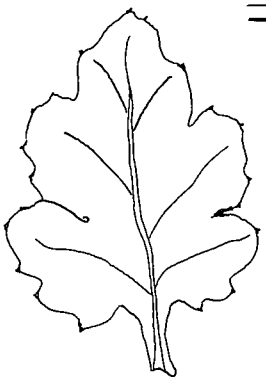

The following is a detailed description of the new variety of chrysanthemum plant with color designations according to the Horticultural Colour Chart issued by the British Colour Council.

*The plant*

Origin: Seedling selected from many random crosses.
Parentage: Unknown.
Classification: Botanic—*Chrysanthemum morifolium*—Commercial—Decorative pot-plant.
Form: Much branched pot-plant.
Height: About 13 to 16 inches.
Growth: Terminal. Vigorous, fairly strong and upright with good branching character.
Foliage: Quantity—Abundant with about 18 leaves per 12 inch stem.

*Leaf size.*—Approximately 3½ to 4½ inches long by about 2½ to 3 inches wide.
*Shape.*—Lobed and serrated with a generally ovate outline.
*Texture.*—Leathery.
*Color.*—Upper side—Spinch Green 960—under side—Spinach Green 960/1.
*Ribs and veins.*—Alternate.
*Petioles.*—Short—½ inch long.

*The bud*

Form: Globular.
Size: Small with ½ inch diameter and ⅜ inch depth.
Opening rate: Bud open slowly—about 2 weeks.
Color: When sepals first divide—Pale Yellow—When petals begin to unfurl—Burnt Orange.
Sepals: Spear shaped and curl back under petals. Color:
*Inside.*—Scheeles Green 860/1.
*Outside.*—Scheeles Green 860/1.
Calyx: Shape — flat-disc — Size — insignificant — aspect—smooth and calyx does not split.
Peduncle: Erect, about 1½ to 2 inches long, and slightly tomentose—Color: Scheeles Green 860/1.

*The flower*

Blooming characteristic: Photoperiod responsive for year-around culture. Natural season, flowering in late October.
Response: 9 week response group.
Blooms: Profusely.
*Size.*—Medium.
*Diameter.*—3 inches (disbudded).
*Depth.*—1 to 2 inches.
*Borne.*—Singly upon disbudding, otherwise as raceme cluster.
*Shape.*—When bloom first open—globular with high center. Form changes later to ball shaped.
*Petalage.*—Low-medium number of petals in composite arrangement (mostly ray petals). Form: ovate and mucronate—color: outer petal—Burnt Orange 0/4—inside petal—Burnt Orange—reverse side—Naples Yellow 430—texture: soft—appearance: satiny.
Peduncle: Upright, about 1½ to 2 inches long—color: Scheeles Green 860/1.
Discoloration: Fades to lighter color after full bloom.
Persistence: Hangs on and dries.
Last quality: Long lasting on plant.

*Reproductive organs*

Stamens: Anthers: few in number, about ¼ inch long, in composite arrangement—filaments: about ¼ inch long—color: Yellow.
Pollen: Color: Indian Yellow.
Pistils: One for each ray floret.
Stigmas: Color—indeterminate.
Characteristics of ovaries: Indeterminate.

*Fruit*

Fertile seeds of ovoid to oblong shape and of brown color at maturity.

The principal distinctions of my new variety of chrysanthemum for greenhouse pot-plant culture reside in its unique coloration which goes from a yellow in the bud stage to a reddish-bronze color in full bloom. The full bloom color appears to be an almost irridescent burnt orange and there is a sprinkling of yellow streaks appearing as the bloom reaches maturity. It is in this respect that the color of this new variety is distinct over all other bronze-red pot chrysanthemums. This new variety is a vigorous grower with fairly strong upright branches which grow to a height of about 13 to 16 inches to produce a short symmetrical plant providing a brilliant display of blooms.

I claim:

1. A new and distinct variety of chrysanthemum plant of the decorative pot-plant type, substantially as herein shown and described, characterized by the almost irridescent burnt orange color of flowers in full bloom, its nine week response under photoperiod culture and its capability of being flowered at anytime of the year to produce short symmetrical plants.

No reference cited.

ROBERT E. BAGWILL, Primary Examiner